United States Patent
Yun et al.

(10) Patent No.: US 10,478,139 B2
(45) Date of Patent: *Nov. 19, 2019

(54) COMPUTED TOMOGRAPHY SYSTEM HAVING COOLING SYSTEM

(71) Applicant: Samsung Electronics Co., Ltd., Gyeonggi-do (KR)

(72) Inventors: Alexander Yun, Gyeonggi-do (KR); Sung-ki Kim, Seoul (KR); Jeong-min Na, Seoul (KR); Il Seong, Gyeonggi-do (KR); Chang-yeon Won, Seoul (KR); Tae-sik Cho, Gyeonggi-do (KR)

(73) Assignee: Samsung Electronics Co., Ltd., Yeongtong-gu, Suwon-si, Gyeonggi-do (KR)

(*) Notice: Subject to any disclaimer, the term of this patent is extended or adjusted under 35 U.S.C. 154(b) by 417 days.

This patent is subject to a terminal disclaimer.

(21) Appl. No.: 15/002,772

(22) Filed: Jan. 21, 2016

(65) Prior Publication Data

US 2016/0235378 A1 Aug. 18, 2016

(30) Foreign Application Priority Data

Feb. 12, 2015 (KR) .................. 10-2015-0021774

(51) Int. Cl.
*A61B 6/00* (2006.01)
*A61B 6/03* (2006.01)
(Continued)

(52) U.S. Cl.
CPC ............ *A61B 6/4488* (2013.01); *A61B 6/035* (2013.01); *H05G 1/025* (2013.01); *A61B 6/0407* (2013.01);
(Continued)

(58) Field of Classification Search
CPC .. A61B 6/00; A61B 6/03; A61B 6/035; A61B 6/44; A61B 6/4447; A61B 6/4488;
(Continued)

(56) References Cited

U.S. PATENT DOCUMENTS 5,761,269 A 6/1998 Sugihara et al.
6,909,775 B2 6/2005 Ray et al.
(Continued)

FOREIGN PATENT DOCUMENTS

JP 10-160847 A 6/1998
KR 1998-050546 U 10/1998
(Continued)

OTHER PUBLICATIONS

Korean Notice of Allowance dated Sep. 8, 2016.
Korean Notice of Non-Final Rejection dated Mar. 3, 2016.

*Primary Examiner* — Anastasia Midkiff
(74) *Attorney, Agent, or Firm* — Cha & Reiter, LLC

(57) ABSTRACT

A cooling system of a computed tomography (CT) system provides for a more efficient operation than known heretofore. The cooling system of the CT system includes a gantry and a table that moves an object into a bore of the gantry. The gantry includes part boxes mounted therein, and blade elements are formed in regions of the part boxes. The cooling system of the CT system includes a cooling method that includes a multiple cooling method including a stand-by mode and an operating mode.

12 Claims, 9 Drawing Sheets

(51) Int. Cl.
*H05G 1/02* (2006.01)
*A61B 6/04* (2006.01)

(52) U.S. Cl.
CPC ..... *A61B 6/4291* (2013.01); *A61B 2560/0406* (2013.01); *H01J 2235/12* (2013.01); *H01J 2235/127* (2013.01); *H01J 2235/1208* (2013.01); *H01J 2235/1216* (2013.01); *H01J 2235/1225* (2013.01); *H01J 2237/002* (2013.01)

(58) Field of Classification Search
CPC ............ A61B 2560/00; A61B 2560/02; A61B 2560/04; A61B 2560/0406; H05G 1/00; H05G 1/02; H05G 1/025; G01N 2223/00; G01N 2223/31; G01N 2223/3103; H01J 2235/12; H01J 2235/1216; H01J 2235/1225; H01J 2235/1245; H01J 2235/125; H01J 2237/002
See application file for complete search history.

(56) References Cited

U.S. PATENT DOCUMENTS

| | | |
|---|---|---|
| 7,311,439 B2 | 12/2007 | Muller |
| 7,410,295 B2 | 8/2008 | Distler et al. |
| 7,851,765 B2 | 12/2010 | Heismann et al. |
| 2004/0114723 A1 | 6/2004 | Ray et al. |
| 2011/0228910 A1 | 9/2011 | Gregerson et al. |
| 2017/0042493 A1* | 2/2017 | Yun ........................ A61B 6/035 |

FOREIGN PATENT DOCUMENTS

| | | |
|---|---|---|
| KR | 2003-0006348 A | 1/2003 |
| KR | 10-2014-0029296 A | 3/2014 |

\* cited by examiner

COMPUTED TOMOGRAPHY SYSTEM HAVING COOLING SYSTEM

CLAIM OF PRIORITY

This application claims the benefit of priority from Korean Patent Application No. 10-2015-0021774, filed on Feb. 12, 2015, in the Korean Intellectual Property Office, the disclosure of which is incorporated by reference herein in its entirety.

BACKGROUND

1. Field of the Disclosure

The present disclosure relates to computed tomography (CT) systems that include a cooling system.

2. Description of the Related Art

With recent advances in medical technology, various methods of obtaining internal information of a living body have been developed. In particular, a tomography system is now widely used. With regard to tomography systems, a computed tomography (CT) system is now in widespread use. The CT system is a device for obtaining an image such that, after irradiating an X-ray toward an object from various angles, the X-ray that passes through the object is measured, and afterwards, the degree of absorption of the X-ray with respect to a cross-section is restructured to generate the image. In a general X-ray image, a three-dimensional (3D) shape of the object is displayed on a two-dimensional (2D) film. However, the CT system can display a 3D shape of a selected cross-section. Accordingly, various points of diagnosis that may not be found from a general X-ray image can be accurately determined if a 3D shape of a selected cross-section is displayed. Due to advantages such as the CT system being able to non-destructively and safely inspect an object, the CT system is widely used not only in medical fields but also in industrial fields to find an internal shape or density of an object.

A gantry of the CT system may include various parts. X-ray generation parts and other various parts of the CT system included in the gantry individually include a cooling system. Each part mounted in the CT system includes at least one fan in a box to cool CT parts. The fans for respective parts and an exhaust fan of the gantry of the CT system may be sources of noise in the overall CT system, and thus, the durability of the CT system may be reduced.

SUMMARY

The present disclosure provides at least one cooling system, cooling apparatus and cooling method of a computed tomography (CT) system, in which the cooling system has blade elements formed inside a gantry and methods of cooling the CT system.

Additional aspects of the present disclosure will be set forth in part in the description which follows and, in part, will be apparent to a person of ordinary skill in the art from the description, and/or may be learned by practice of the presented embodiments by the person of ordinary skill in the art.

According to an aspect of the present disclosure, in a cooling system of a CT system, the cooling system includes a gantry and a table that moves an object into a bore of the gantry, wherein the gantry comprises a part box mounted therein, and additionally includes blade elements that are formed/arranged in regions of the part box and control an air flow inside the gantry.

The part box may include inlet holes and exhaust holes, and the blade elements may be formed/arranged in the inlet holes.

One edge of each of the blade elements may be exposed on a surface of the part box through the inlet hole, and another edge of each of the blade elements extends towards an inner side of the inlet hole of the part box.

The blade elements may be formed over the exhaust holes.

The gantry may include a rotor that rotates with the bore as a center and a stator that does not rotate, and the part box may be mounted in the rotor.

The blade elements may include a first blade element formed in the rotor and a second blade element formed in the stator.

The first blade element may be directly formed on a housing of the part box and the rotor.

The cooling system of the CT system may further include an exhaust fan formed together with the at least one blade element.

The part box may include hardware such as an X-ray generator, an X-ray detector, and at least one of a data acquisition system (DAS), a power supplier, a heat exchanger (HX), an HVG, and a wireless transducer just to name some non-limiting examples.

According to an aspect of another exemplary embodiment, a method of cooling the CT system described above includes a stand-by mode in which the gantry is cooled by exhaust fans mounted in the gantry in the event that a rotor of the gantry is not rotating; and an operating mode in which the gantry is cooled by blade elements formed inside the gantry when the rotor of the gantry rotates.

In the operating mode, all of the exhaust fans or at least some of the exhaust fans may be stopped.

BRIEF DESCRIPTION OF THE DRAWINGS

The patent or application file contains at least one drawing executed in color. Copies of this patent or patent application publication with color drawings will be provided by the U.S. Patent and Trademark Office upon request and payment of the necessary fee.

The above and/or other aspects of the present disclosure will become more better understood and more readily appreciated by a person of ordinary skill in the art from the following description of the exemplary embodiments, taken in conjunction with the accompanying drawings in which:

FIG. 3A and FIG. 3B are perspective views of blade elements formed parts mounted inside the gantry of the cooling system of a CT system according to an embodiment, wherein FIG. 3A is a perspective view with in holes in lateral sides of a parts box, and FIG. 3B shows the holes within front and rear sides of the part box;

DETAILED DESCRIPTION

Figure 1:
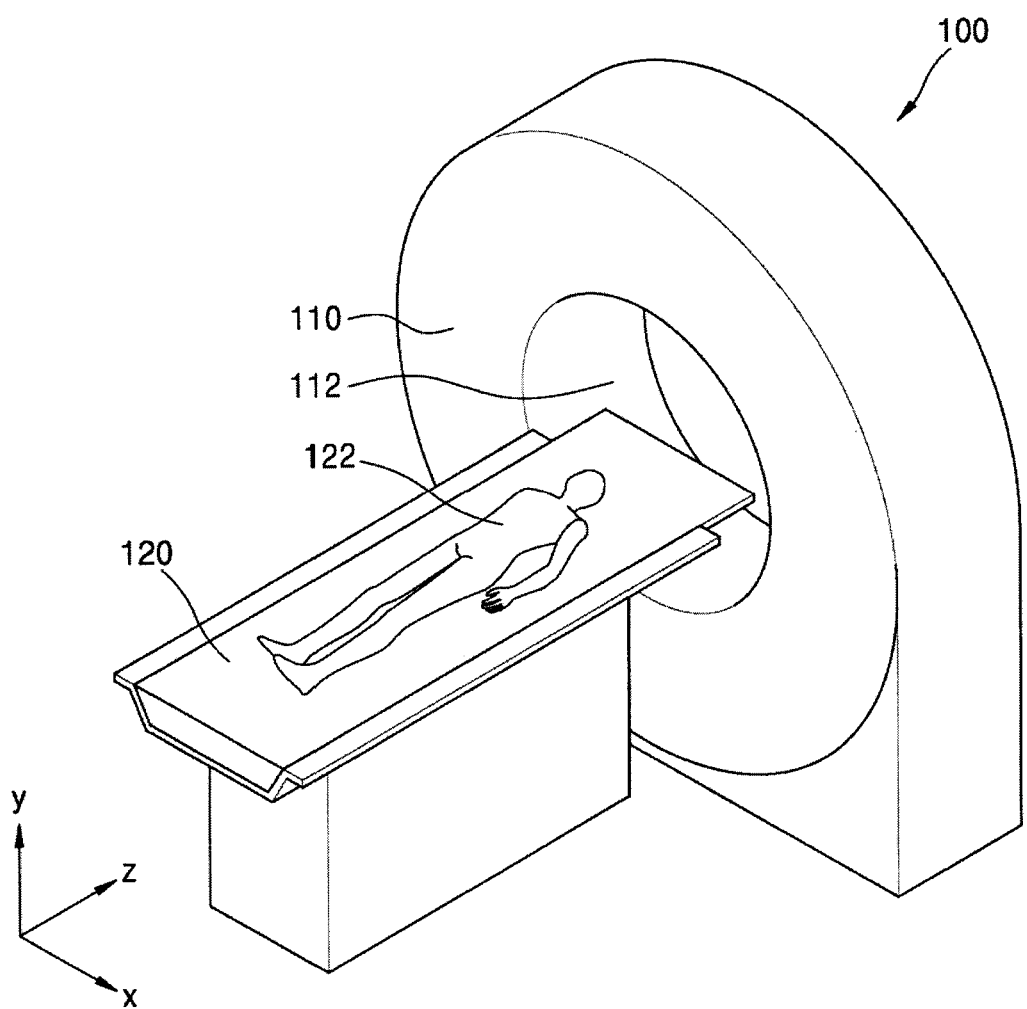
FIG. 1 is a perspective view of a cooling system of a computed tomography (CT) system according to an embodiment of the disclosure.

A cooling system of a computed tomography (CT) system will now be described in detail with reference to certain embodiments, examples of which are illustrated in the accompanying drawings. An artisan will understand and appreciate that the appended claims are not limited to the aspects of the disclosure shown in the drawings. In the drawings, like reference numerals refer to like elements throughout and elements having the same numeral may be formed of the same material. Also, in the drawings, sizes of elements may be exaggerated for convenience and clarity of explanation.

FIG. 1 is a schematic perspective view of a CT system 100 according to an embodiment of the disclosure.

Referring now to FIG. 1, the CT system 100 according to an embodiment may include a gantry 110 having a cylindrically shaped bore 112 in a center thereof and a table 120 that transports an object 122 (such as a patient) to be examined into and out of the bore 112 of the gantry 110. The object 122 may be moved into the bore 112 of the gantry 110 by being positioned on the table 120. The table 120 may be moved in various directions, for example, in at least one of up, down, left, and right directions in the course of capturing a CT image, and also, may be tilted or rotated at a predetermined angle in a particular direction. Also, the gantry 110 may be tilted in a specific direction by a desired predetermined angle.

The object 122 may include a human or an animal, or part of a human or animal. For example, the object 122 may include organs such as a heart, liver, brain, breast, uterus, abdominal organ, spinal cord, or blood vessel. Also, the object 122 may include a phantom. The phantom may denote a material having a volume near to a density of a living thing and an actual effective atomic number, and may include a spherical phantom having a characteristic similar to a body.

The gantry 110 may include a stator that does not rotate and a rotor that includes an X-ray generator and various parts. Parts included in the gantry 110 may be an X-ray generator, an X-ray detector, a data acquisition system (DAS), a power supply, a heat exchanger (HX), a high voltage generator (HVG), etc., and these parts may be mounted in a cover of the gantry 110. When the CT system 100 is operated, the temperature inside the gantry 110 typically increases versus the temperature-of a standby mode due to the operation of the parts in the gantry 110. The increase in the temperature of the gantry 110 may be a cause of noise in the whole CT system 100, and may reduce the durability of the whole CT system 100. In the CT system 100 according to an embodiment, blade elements are formed in the parts, the stator, or the rotor to control air flow in the gantry 110, and thus, the temperature of the gantry 110 may be maintained at an appropriate level so as not to cause discomfort to a patient or possibly damage the electronic equipment.

Figure 2:
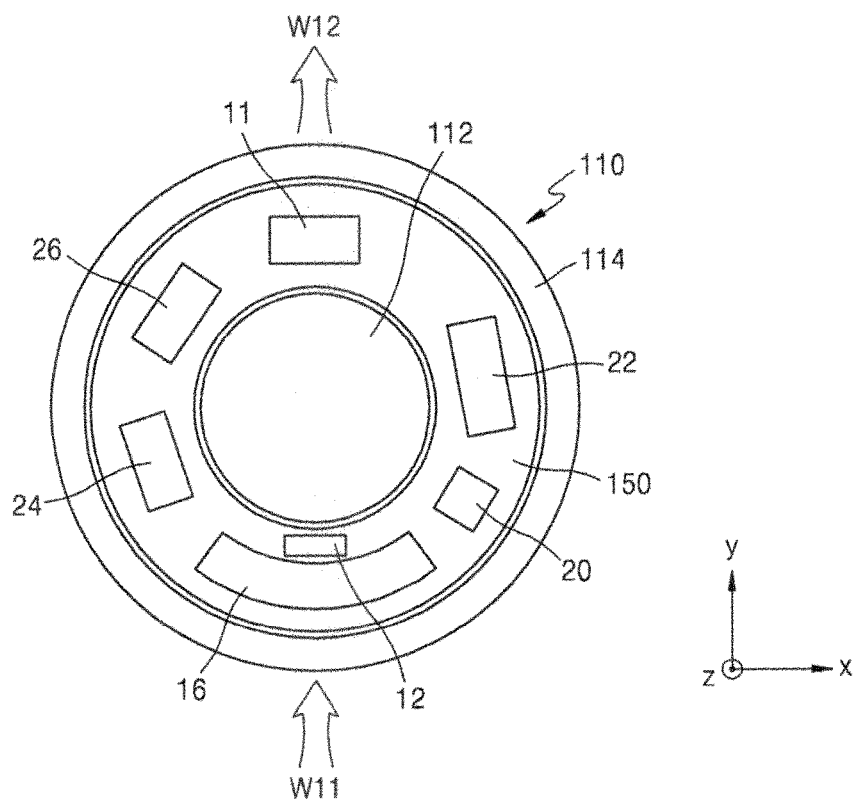
FIG. 2 is a plan view of inside of a gantry of the cooling system of a CT system according to an embodiment of the disclosure.

FIG. 2 is a schematic plan view of inside of the gantry 110 of the CT system 100 according to an embodiment.

Referring now to FIG. 2, the gantry 110 may include a rotor 150 that rotate with respect to a stator 114, and the rotor has the bore 112 as a center. The stator 114 is formed around the rotor 150 and does not move. Various parts for operating the CT system 100 may be mounted in the rotor 150. For example, the parts may be an X-ray generator 11, an X-ray detector unit 12, and a DAS 16. Besides the above hardware, a power supply, a heat exchanger (HX), a high voltage generator (HVG), and a wireless transducer may also be mounted on the rotor 150. The parts in the gantry 110 may have a box-type external shape formed of, for example, a metal or plastic or a box-type housing. Hereinafter, in the embodiment, these are referred to as part boxes including the box-type and the housing mounted in the gantry 110.

Reference numerals 20, 22, 24, and 26 indicate the various part boxes that may be mounted in the gantry 110. The parts in the gantry 110 may generate heat during the operation of the cooling system of the CT system 100. When the cooling system of the CT system 100 continuously operates at a high temperature, the durability and performance of the cooling system of the CT system 100 may be reduced, and thus, a cooling system to reduce the temperature is preferable and may be necessary. In order to maintain an inner temperature of the gantry 110 at an appropriate level, the external air may be taken into and circulated in the rotor 150 of the gantry 110 by receiving external air W11 from at least a side of the gantry 110, and the circulated air may be exhausted W12 to the outside of the gantry 110. In FIG. 2, as an example, it is depicted that the external air is supplied W11 from a lower side of the gantry 110 and is exhausted W12 to the upper side of the gantry 110. However, the current embodiment is not limited thereto, that is, the direction of entering the external air and the direction of exhausting the external air are not specifically limited to the illustration of FIG. 2.

Figure 3A:
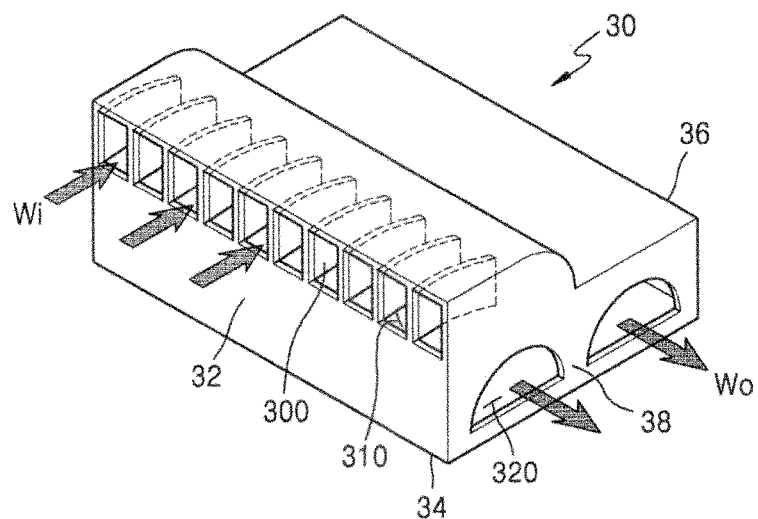
Figure 3B:
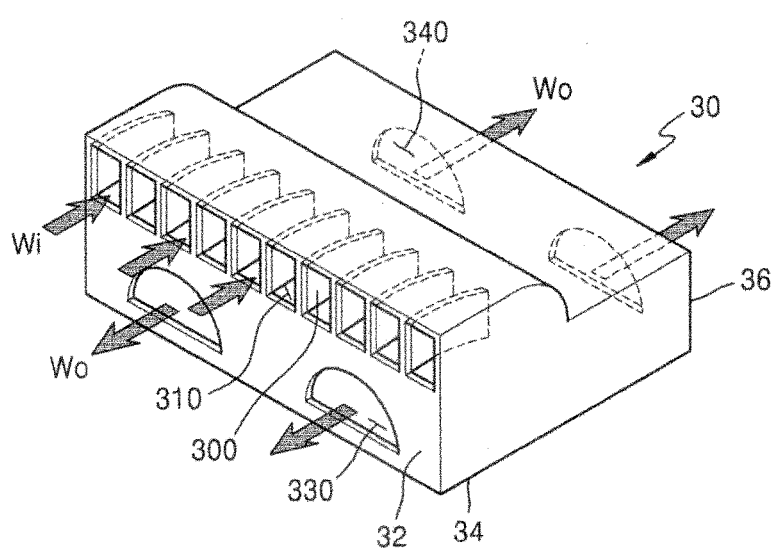
Figure 3C:
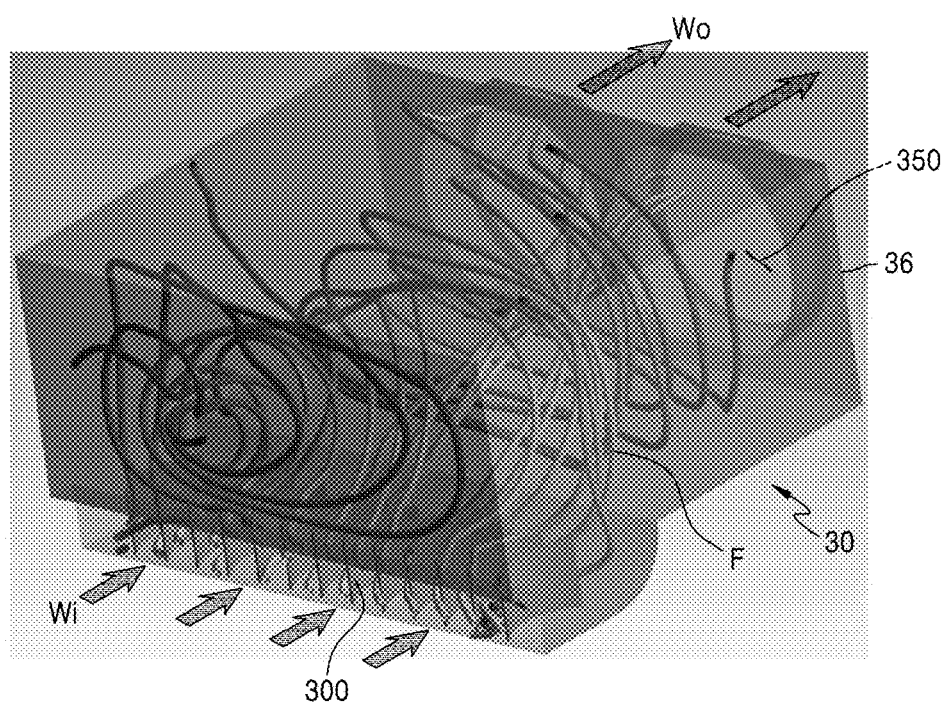
FIG. 3C is a schematic drawing showing an air flow in the parts box due to the arrangement of blade elements.

FIGS. 3A and 3B are perspective views of blade elements formed in parts mounted inside the gantry 110 of the cooling system of the CT system 100 according to an embodiment. FIG. 3C is a schematic drawing showing an air flow due to the blade elements.

Referring now to FIGS. 2 and 3A, a part box 30 mounted in the rotor 150 of the gantry 110 may include inlet holes 310 through which external air enters into the part box 30 and an exhaust hole 320 through which air in the part box 30 is exhausted to the outside of the part box 30. The part box 30 may be mounted in the rotor 150 of the gantry 110, and the rotor 150 may rotate in a clockwise direction with the bore 112 as a center. The part box 30 in the rotor 150 also rotates in the clockwise direction as the rotor 150 rotates. Each of the inlet holes 310 may include at least one blade element 300. An edge of each blade element 300 may be exposed to a surface of the part box 30 through the inlet holes 310, and another edge of each blade element 300 may be attached to an inner wall of the part box 30 by extending into the inlet holes 310 of the part box 30. The blade element 300 may control the flow direction of air in the gantry 110. External air may be supplied Wi into the part box 30 through the inlet holes 310 by the blade element 300. The external air that circulates in the part box 30 to cool the part box 30 may be exhausted Wo to the outside of the part box 30 through the exhaust hole 320.

The blade element 300 may be formed in the inlet holes 310 of the part box 30. And the inlet holes 310 may be formed at least in a region of the part box 30 but the location of the inlet holes 310 is not specifically limited to the location shown in the drawings. Also, the location of the exhaust hole 320 is not specifically limited to the location shown in the drawings. For example, the inlet holes 310 and the exhaust hole 320 may be formed on a lower surface 34 of the part box 30, a rear surface 36 of the part box 30, and a lateral surface 38 of the part box 30. Also, the location of the exhaust hole 320 may be formed at least on a side of the part box 30. In FIG. 3A, as an example, the exhaust hole 320 is formed only in the lateral surface 38 of the part box 30. In FIG. 3B, a structure, in which exhaust holes 330 are formed on a front surface 32 of the part box 30 and exhaust holes 340 are formed on the rear surface 36 of the part box 30, is shown. In this manner, external air may be supplied Wi into the part box 30 due to the at least one blade element 300 formed on the inlet holes 310 of the part box 30, and the external air supplied into the part box 30 may exhaust Wo heat in the part box 30 to the outside through the exhaust holes 330 and 340.

FIG. 3C shows a simulation result of air circulation in the part box 30 after external air is supplied Wi through the inlet holes 310 (the inlet holes 310 also shown in FIGs.3A and 3B. Here, the part box 30 is mounted in the rotor 150 of FIG. 2 and is rotated at a speed of approximately 240 revolutions per minute (rpm).

Referring now to FIG. 3C, after entering through the inlet holes 310, the external air may proceed towards the exhaust holes 350 while supplying air to the part box 30 due to blade elements 300. The external air supplied to the part box 30 may move to the outside through the exhaust holes 350 after flowing F in the part box 30 to cool the part box 30. At this point of the simulation, air in the part box 30 showed a mass flow of approximately 145 cubic feet per minute (CFM).

Figure 4A:
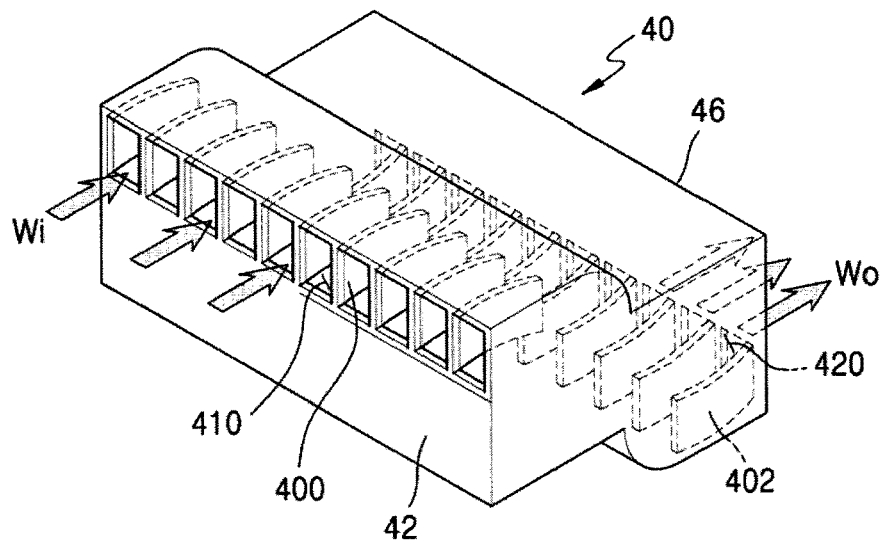
FIG. 4A is a perspective view of blade elements respectively formed in an intake port and an exhaust port of a part box mounted inside the gantry of the cooling system of a CT system according to an embodiment of the disclosure.
Figure 4B:
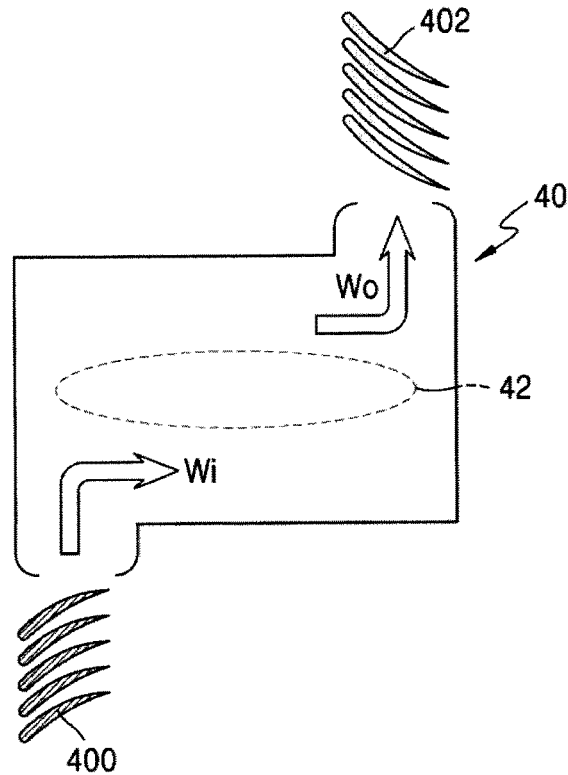
FIG. 4B is a schematic view illustrating a principle of air flow when the blade elements are formed in the intake port and an exhaust port of FIG. 4A.

FIG. 4A is a perspective view of blade elements 400 respectively formed in an inlet hole 410 and an exhaust hole 420 of the part box 40 mounted inside the gantry of the cooling system of the CT system 100 according to an embodiment of the disclosure. FIG. 4B is a schematic view illustrating a principle of air flow when the blade elements 400 are formed in the inlet hole and the exhaust hole of FIG. 4A.

Referring now to FIG. 2 and FIG. 4A, at least one blade element 400 may be formed on an inlet hole 410 of the part box 40 mounted in the rotor 150 of the gantry 110. Also, at least another blade element 402 may be formed on an exhaust hole 420 of the part box 40. In FIG. 4A, as an example, the inlet holes 410 are formed on a front surface 42 of the part box 40 and the exhaust holes 420 are formed on a rear surface 46 of the part box 40, but the current embodiment is not limited to the arrangement shown and described. An edge of the blade element 402 formed on the exhaust hole 420 may be exposed and fixed on a portion of an inlet of the exhaust hole 420 and another edge of the blade element 402 may be formed by extending from the exhaust hole 420. The blade element 402 may be fixed on the exhaust hole 420 and on an inner surface of the part box 40. The blade elements 400 and 402 respectively formed on the inlet holes 410 and the exhaust hole 420 may be bent to have curvatures, but such as structure is not limited to the depiction in the drawings, and also, the shape and size of the elements are not specifically limited to the items shown. The number of blade elements 400 and 402 formed on the inlet holes 410 and the exhaust hole 420 is not specifically limited to any particular number.

When the rotor 150 of the gantry 110 rotates, for example, in a clockwise direction, the part box 40 mounted on the rotor 150 also rotates in the same direction as it is attached to the rotor.

Referring now to FIG. 4B, as the part box 40 rotates according to the rotational movement of the rotor 150, external air may be supplied Wi into the part box 40 through the inlet holes 410 and air in an inner space 42 of the part box 40 may be exhausted Wo to the outside of the part box 40 through the blade element 402 formed on the exhaust hole 420. The pressure of the inner space 42 of the part box 40 may be lower than regions of the inlet holes 410 and the exhaust hole 420.

Figure 5:
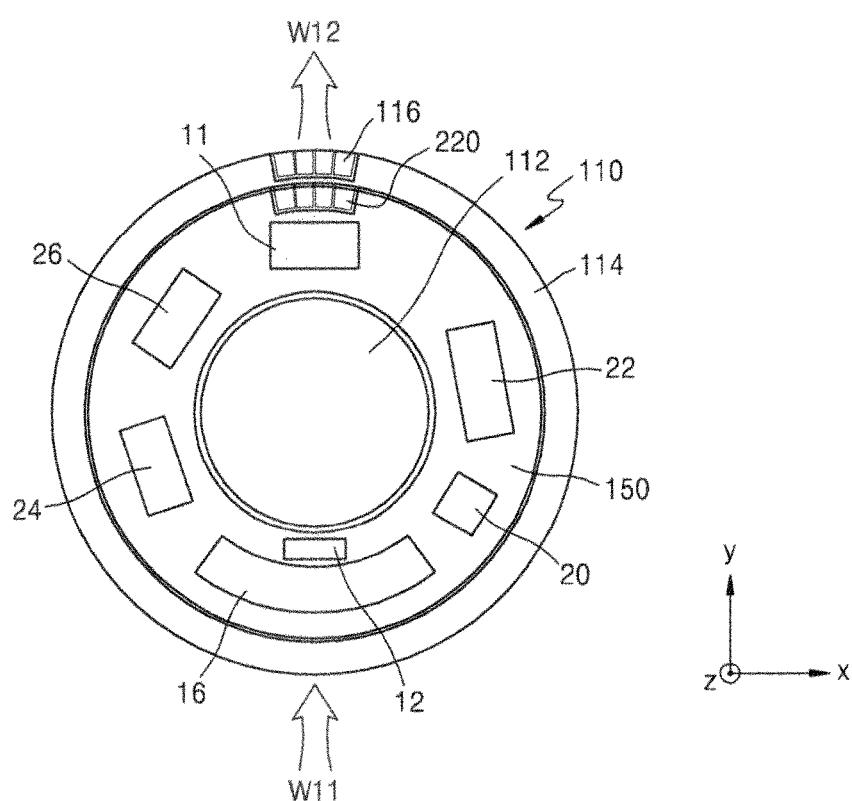
FIG. 5 is a schematic drawing of a blade element mounted in a gantry of a cooling system of a CT system according to an embodiment of the disclosure.

FIG. 5 is a schematic drawing of a blade element mounted in the gantry 110 of the cooling system of the CT system according to an embodiment of the disclosure. Referring now to FIG. 5, the gantry 110 may include a rotor 150 that rotates, and the rotor 150 has a bore 112 as a center. A stator 114 that is formed around the rotor 150 does not rotate. Blade elements 220 may be formed on the rotor 150 of the gantry 110 and blade elements 116 may also be formed on the stator 114. At least one blade element may be respectively formed of the rotor150 and the stator 114. In this manner, the blade elements may be formed not only on a part box of the rotor 150, but also may be directly formed on a housing of the rotor 150 and the stator 114.

The blade elements 220 formed on the part box or the housing of the rotor 150 may be referred to as a first blade element, and the blade elements formed on the stator 114 may be referred to as a second blade element. External air may be supplied W11 in an inner direction of the gantry 110 from the outside of the gantry 110, and may enter into the rotor 150 through the first blade element 220 of the rotor 150 or may be exhausted to the outside of the rotor 150 from the inside of the rotor 150. The second blade element 116 formed on the stator 114 may exhaust W12 the air in the stator 114 to the outside. In this way, the first and the second blade elements 220 and 116 respectively may be formed on the rotor 150 and the stator 114 of the gantry 110, and the first blade element 220 formed on the rotor 150 may be formed on the part box or a housing region of the rotor 150. The blade elements 220 and 116 of the rotor 150 and the stator 114 may be formed together with an additional exhaust fan. Also, exhaust fans may be optionally formed on the part boxes 30 and 40 shown in FIGS. 3A, 3B, and 4A. However, the at least one exhaust fan mounted in the gantry 110 is not normally operated, and may be in a stand-by mode at which the rotor 150 of the gantry 110 is stopped until, for example, the temperature rises to a certain threshold.

Figure 6A:
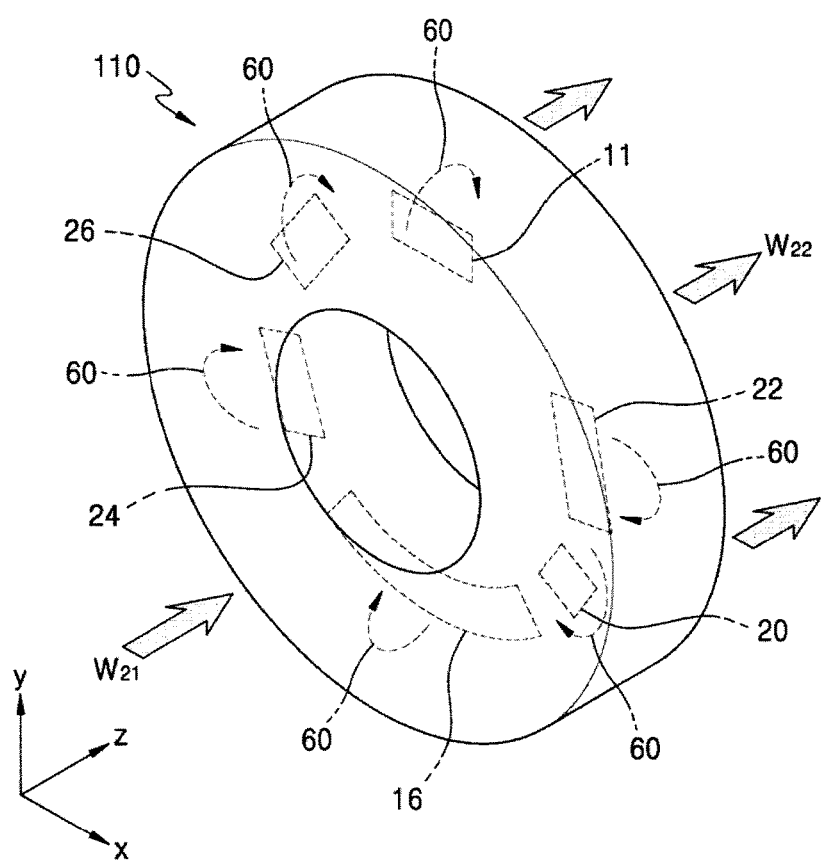
FIG. 6A is a perspective view illustrating a stand-by mode of the cooling system in a method of driving a cooling system of the CT system according to an embodiment of the disclosure
Figure 6B:
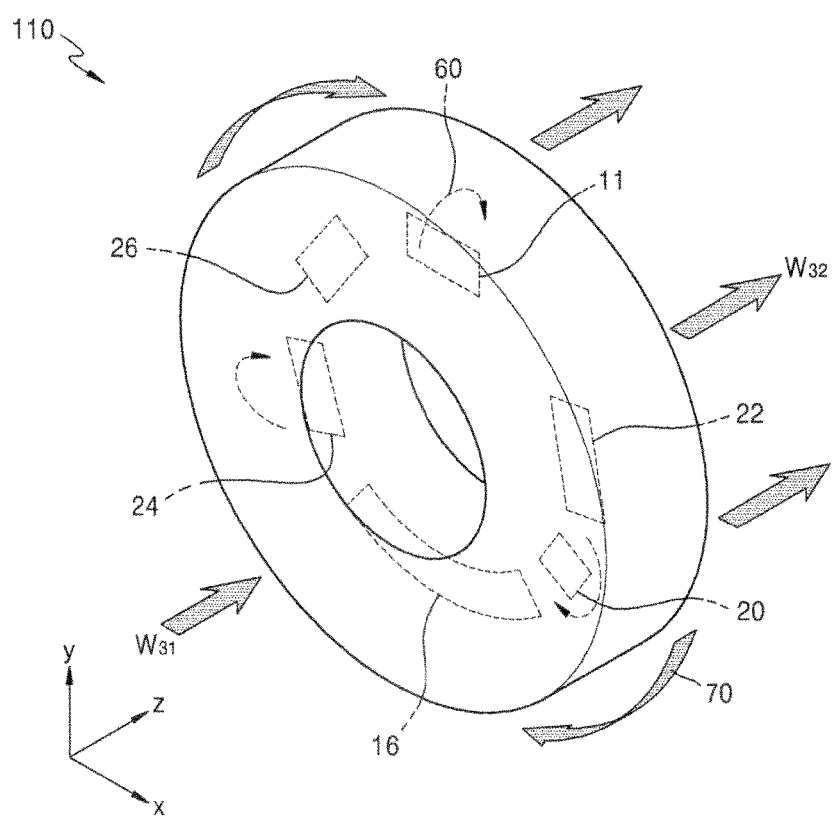
FIG. 6B is a perspective view illustrating an operating mode of the cooling system in a method of driving a cooling system of the CT system according to an embodiment of the disclosure.

FIGS. 6A and 6B are perspective views illustrating methods of driving a cooling system of the CT system 100 according to an embodiment. FIG. 6A shows a stand-by mode of the cooling system of the CT system 100, and FIG. 6B shows an operating mode of the cooling system of the CT system 100.

Referring now to FIGS. 5 and 6A, in the stand-by mode, the rotor 150 of the gantry 110 does not move (i.e. is not in a rotation state). In this state, an exhaust fan 60 mounted in a plurality of part boxes 11, 16, 20, 22, 24, and 26 or in the gantry 110 is operated, and thus, external air may be supplied W21 into the gantry 110 via the exhaust fan without rotation of the rotor. The inside of the gantry 110 may be cooled down by the low temperature air that is supplied from the outside, and the internal air of the gantry 110 may be exhausted W22 to the outside of the gantry 110. This cooling, in which the fan is operation while the rotor is stationary, is referred to as a stand-by mode cooling method. In the stand-by mode cooling method, the air circulation in the gantry 110 may be achieved while operating the exhaust fans in the gantry 110 together with the blade elements 220 and 116, and thus, the cooling efficiency of the gantry 110 may be increased, yet no energy is expended to spin the rotor 150.

Referring now to FIGS. 5 and 6B, in the operating mode, the rotor 150 of the gantry 110 may rotate, for example, in a clockwise direction 70. Along with the rotating movement of the rotor 150, external air outside the gantry 110 may be supplied W31 to the gantry 110 by the blade elements 220 and 116 in the gantry 110 and the blade elements formed in the plural part boxes 11,16, 20, 22, 24, and 26. The inside of the gantry 110 may be cooled by the low temperature air supplied from the outside. Also, the internal air of the gantry 110 may be exhausted W32 to the outside of the gantry 110. At this point, the operation of all of the exhaust fans in the gantry 110 may stop or some of the exhaust fans 60 may continue to be operated. This mode of operation is referred to as an operating mode. Unlike the stand-by mode cooling method, in the operating mode, the noise or interference phenomenon due to the exhaust fans may be prevented by stopping the operation of the exhaust fans or by operating some of the exhaust fans of the gantry 110 and rotating the rotor, and thus, the cooling efficiency of the gantry 110 may be increased.

In the cooling system of the CT system 100 according to an embodiment, the flow direction of air inside the gantry 110 may be controlled by forming blade elements on the rotor 150, the stator 114, or the part boxes 30 and 40. The insides of the part boxes 30 and 40 may be cooled by forming blade elements in the part boxes 30 and 40, such as, the X-ray generation unit 11, an X-ray detection unit 12, the DAS 16, the power supply, the HX, the HVG, and the wireless transducer. Optionally, additional exhaust fans may not be formed on the part boxes 30 and 40. In the cooling system of the CT system 100 according to an embodiment, an inner space of the gantry 110 may be more efficiently managed and operated by minimizing the number of fans mounted in the gantry 110, and thus, noise of the CT system 100 may be prevented. Accordingly, the durability of the CT system 100 may be increased.

Figure 7:
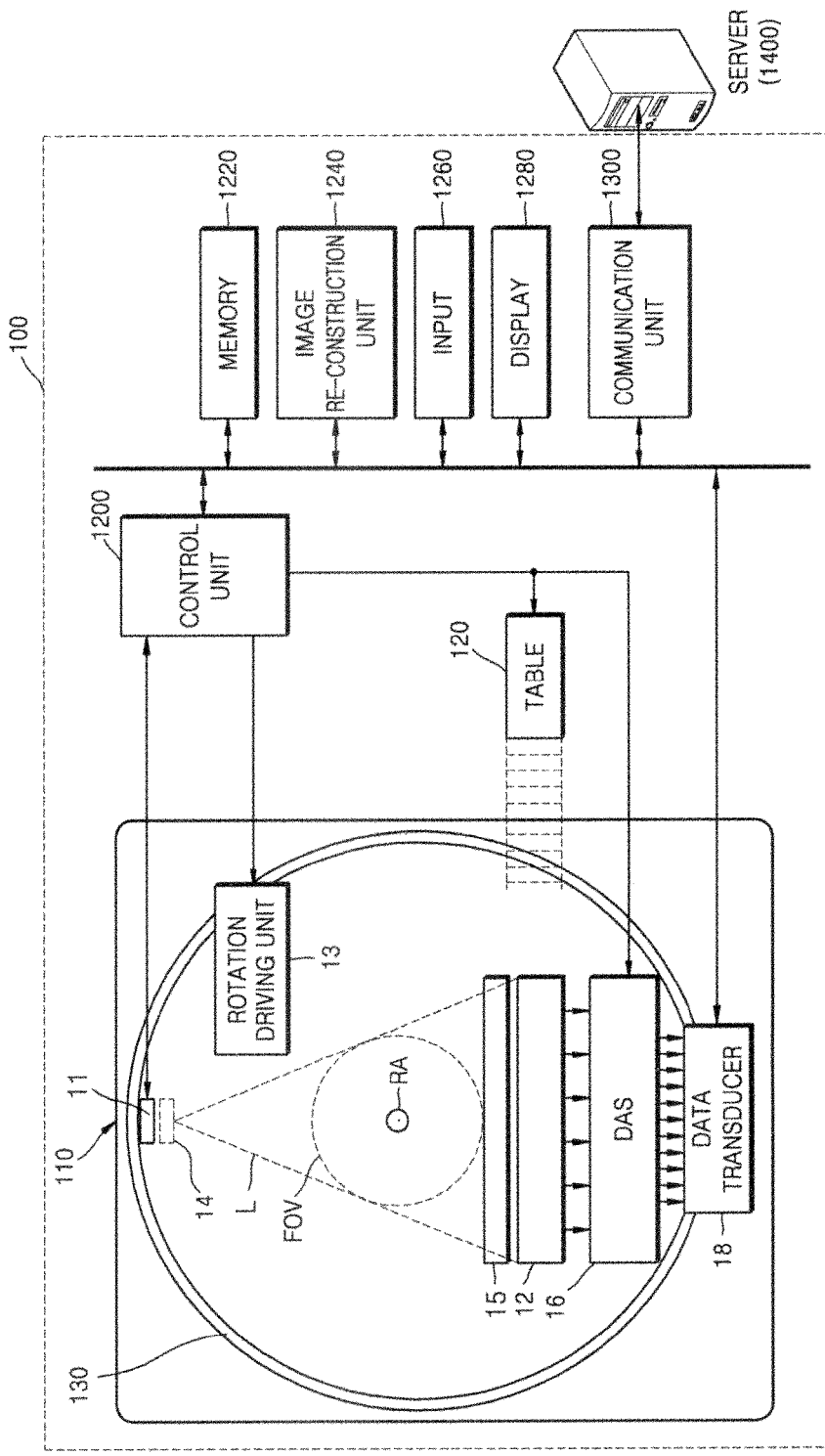
FIG. 7 is a schematic showing an overall configuration of a cooling system of a CT system according to an embodiment of the disclosure.

FIG. 7 is a schematic showing an overall configuration of the cooling system of the CT system 100 according to an embodiment.

Referring now to FIGS. 1 and 7, the cooling system of the CT system 100 according to an embodiment may include a gantry 110, a table 120, a controller 1200 including hardware configured for operation, such as an integrated circuit of a microprocessor or processor, a storage unit 1220 (i.e. a non-transitory memory), an image re-construction unit 1240, an input 1260, a display 1280, and a communication unit 1300 including hardware such as a transmitter, receiver, transceiver and antenna. The object 122 may be positioned on the table 120, and the table 120 may move in at least a predetermined direction and back, for example, up, down, left, and right directions by being controlled by the control unit 1200. The gantry 110 may include an X-ray generator 11, a collimator 14, an X-ray detection unit 12, a rotation driving unit 13, a DAS 16, and a data transducer 18. The gantry 110 may include an annular type rotation frame 130 that is rotatable with respect to a predetermined rotation axis (RA). The rotation frame 130 may include the X-ray generator 11 and the X-ray detector12 that are respectively facing each other to have a predetermined field of view (FOV). Also, the rotation frame 130 may include an anti-scatter grid 15. The anti-scatter grid 15 may be located between the X-ray generator 11 and the X-ray detector 12. The rotation frame 130 may receive a driving signal from the rotation driving unit 13 and may rotate the X-ray generator 11 and the X-ray detector 12 at a predetermined speed. The rotation frame 130 may receive a driving signal and power from the rotation driving unit 13 in a contact method through, for example, a slip ring. The rotation frame 130 may receive a driving signal and power from the rotation driving unit 13 via wireless communication.

In a medical imaging system, not only does an attenuated primary radiation signal form a useful image but also the scattered radiation that reduces the quality of image may be included in an X-ray that reaches the X-ray detector unit 12 (or photo-sensitive film). In order to transmit majority of the primary radiation and to attenuate the scattered radiation, the anti-scatter grid 15 may be located between the object 122 and the X-ray detector 12. The anti-scatter grid 15 may be formed in a type in which interspace materials, such as, strips of a lead foil and a solid polymer material without a hollow or a solid polymer and a fiber composite material without a hollow are alternately stacked. However, the configuration of the anti-scatter grid 15 is not necessarily limited thereto.

The object 122 may be moved into the bore 112 of the gantry 110 by being positioned on the table 120 and moving the table. An X-ray "L" generated from the X-ray generator 11 may be irradiated onto the object 122 through the collimator 14, and the X-ray L that passes through the object 122 may be detected by the X-ray detector 12, and thus, state information of the object may be obtained.

The X-ray generator 11 may generate and emit an X-ray by receiving a voltage and a current, for example, from a power distribution unit (PDU) through a high voltage generation unit via a slip ring. When the high voltage generation (HVG) unit applies a predetermined voltage, the X-ray generator 11 may generate X-rays having a plurality of energy spectrums corresponding to the predetermined voltage. The X-rays generated from the X-ray generator 11 may be emitted as a predetermined state by the collimator 14. The X-ray generator 11 may be configured to include various X-ray generation structures, and may include a plurality of electron emission sources. For example, the X-ray generator 11 may include electron emission sources that may emit electrons and an electrode that may emit X-rays due to the collision between emitted electrons and is formed of a conductive material. The electron emission sources may be formed of a material that may emit electrons, for example, a metal, silicon, an oxide, diamond, diamond like carbon (DLC), a carbon compound, a nitrogen compound, carbon nanotube, etc. The X-ray generator unit 11 may be formed by including a plurality of electron emission sources formed as a ring type. The X-ray generator 11 may change its location during an operation of the gantry 110 but may be fixedly disposed not to be rotated. Also, the X-ray generator 11 may be configured so that an electron gun may irradiate an X-ray in a direction towards the bore 112 of the gantry 110. However, the configuration of the X-ray generator 11 is not limited thereto, that is, may be any configuration as long as the X-ray generator 11 may emit an X-ray.

The X-ray detector 12 may include one or a plurality of X-ray detectors to detect an X-ray that is radiated from the X-ray generator 11 and is passed through the object 122 through the collimator 14 and the X-ray detectors may form an array structure. The X-ray detectors may form a single channel, but is not limited thereto. The X-ray detectors 12 may include a multi-layer structure including a semiconductor layer and an electrode. The X-ray detectors 12 may be formed as a ring shape as the same shape as the X-ray generator 11 on a lateral of the X-ray generator 11. The X-ray detector unit 12 may change its location during an operation of the gantry 110 but may be fixedly disposed not to be rotated. Also, the X-ray detector 12 may detect an X-ray that is generated from the X-ray generator 11 and is transmitted through the object 122 and may generate an electrical signal corresponding to the intensity of the detected X-ray.

The X-ray detector 12 may be connected to the DAS 16. An electrical signal generated from the X-ray detector 12 may be collected by the DAS 16. The electrical signal generated by the X-ray detector 12 may be collected at the DAS 16 either with or without wire. Also, the electrical signal generated by the X-ray detector 12 may be provided to, for example, an analogue/digital converter through an amplifier. Only some of data collected from the X-ray detector 12 may be provided to the image re-construction unit 1240 according to slice thicknesses or number of slices, or some of the data may be selected by the image re-construction unit 1240. The digital signal may be provided to the image re-construction unit 1240 through the data transducer 18. The digital signal may be transmitted to the image re-construction unit 1240 through the data transducer 18 either with or without wire.

The control unit 1200, which comprises hardware configured for operation may control an operation of each module of the cooling system of the CT system 100. For example, the control unit 1200 may control operations of the table 120, the collimator 14, the rotation driving unit 13, memory 1220, the image re-construction unit 1240, the input 1260, the display 1280, and the communication unit 1300. The image re-construction unit 1240 may receive data (for example, pure data before processing) obtained by the DAS 16 through the data transducer 18, and may perform a pre-processing process. The pre-processing may include a process of correcting non-uniform sensitivity between channels and a process of correcting signal loss due to rapid reduction of signal intensity or an X-ray absorbent, such as, a metal. An output data of the image re-construction unit 1240 may be referred to as a raw data or a projection data. The projection data may be stored in the storage unit 1220 together with image capturing conditions (for example, a tube voltage, an image capturing angle, etc.) when the image is captured. The projection data may be a set of data values corresponding to the intensities of X-rays that have passed through the object 122. The storage unit 1220 may include a storage medium at least one of a flash memory type, a hard disk type, a multimedia card micro type, a card type memory (SD, XD memory, etc.), a random access memory (RAM), a static random access memory (SRAM), a read-only memory (ROM), an electrically erasable programmable read-only memory (EEPROM), a programmable read-only memory (PROM), a magnetic memory, a magnetic disc, and an optical disc, just to name a few non-limiting possibilities.

Also, the image re-construction unit 1240 may reconstruct cross-sectional images of the object 122 by using an obtained projection data set. The cross-sectional image may be 3 dimensional (3D) images. In other words, the image re-construction unit 1240 may generate a 3D image of the object 122 by using a cone beam reconstruction method based on the obtained projection data set. An external input with respect to X-ray tomography conditions, image processing conditions, etc. may be received through the input 1260. For example, the X-ray tomography conditions may include a plurality of tube voltages, the setting of energy values of a plurality of X-rays, the selection of shooting protocols, the selection of method of image reconstruction, the setting of a FOV region, the number of slices, slice thicknesses, and the setting of parameters for image post-processing, etc. Also, the image processing condition may include the resolution of image, the setting of attenuation coefficient with respect to an image, and the setting of combination ratio of the image, etc. The input unit 1260 may include a device for receiving an application of a predetermined pressure from the outside. For example, the input 1260 may include a microphone, a keyboard, a mouse, a joystick, a touch pad, a touch pen, a voice, and a gesture recognition device, etc. The display 1280 may display an image restructured by the control image re-construction unit 1240. Transmission and reception of data or power between the elements described above may be performed by using at least one of wires, wireless, and optical communication. The communication unit 1300 may perform communications with an external device or an external medical device through a server 1400.

In the cooling system of a CT system according to an embodiment, blade elements are formed on part boxes, a rotor, or a stator of a gantry, and thus, an air flow in the gantry may be controlled.

In the cooling system of a CT system according to an embodiment, the number of fans formed inside the gantry is minimized, and thus, an inner space of the gantry is efficiently managed and operated. Also, the noise problem of the cooling system of a CT system is reduced and the durability of the CT system is increased.

While a cooling system of a CT system according to THE embodiment has been described with reference to the figures. However, it will be understood by those of ordinary skill in the art that the embodiments should be considered in descriptive sense only and not for purposes of limitation. Also, it should be understood, however, that the appended claims are not limited to the embodiments shown and disclosed herein, but on the contrary, the appended claim include all modifications, equivalents, and alternatives falling within the scope of the disclosure as understood by a person of ordinary skill in the art.

The apparatuses and methods of the disclosure can be implemented in hardware, and in part as firmware or via the execution of software or computer code in conjunction with hardware that is stored on a non-transitory machine readable medium such as a CD ROM, a RAM, a floppy disk, a hard disk, or a magneto-optical disk, or computer code downloaded over a network originally stored on a remote recording medium or a non-transitory machine readable medium and stored on a local non-transitory recording medium for execution by hardware such as a processor, so that the methods described herein are loaded into hardware such as a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc., that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. In addition, an artisan understands and appreciates that a "processor", "microprocessor" "controller", or "control unit" constitute hardware in the claimed disclosure that contain circuitry that is configured for operation. Under the broadest reasonable interpretation, the appended claims constitute statutory subject matter in compliance with 35 U.S.C. § 101 and none of the elements are software per se. No claim element herein is to be construed under the provisions of 35 U.S.C. 112, sixth paragraph, unless the element is expressly recited using the phrase "means for".

The definition of the terms "unit" or "module" as referred to herein are to be understood as constituting hardware circuitry such as a CCD, CMOS, SoC, AISC, FPGA, a processor or microprocessor (a controller) configured for a certain desired functionality, or a communication module containing hardware such as transmitter, receiver or transceiver, or a non-transitory medium comprising machine executable code that is loaded into and executed by hardware for operation, in accordance with statutory subject matter under 35 U.S.C. § 101 and do not constitute software per se. For example, the image processor in the present disclosure, and any references to an input unit and/or an output unit both comprise hardware circuitry configured for operation.

What is claimed is:

1. A cooling system of a computed tomography (CT) system, comprising:
   a gantry having a bore therein; and
   a table that moves into and out of the bore of the gantry,
   wherein the gantry comprises a part box mounted therein, and blade elements that are formed in regions of the part box are arranged to control an air flow inside the gantry,
   wherein the part box is an external housing for a part,
   wherein the part comprises one or more of an X-ray generator, an X-ray detector, a data acquisition system (DAS), a power supplier, a heat exchanger (HX), an high voltage generator (HVG),or a wireless transducer for each part box,
   wherein the part box comprises an inlet hole and an exhaust hole arranged in one or more surfaces of the part box, and the blade elements are fixed on an inner surface of the part box,
   wherein one edge of each of the blade elements is exposed at a surface of the part box through the inlet hole, and another edge of each of the blade elements extends toward an inner side of the inlet hole of the part box, and
   wherein an extended portion between the one edge and the another edge in each of the blade elements is not visible through the inlet hole of the part box.

2. The cooling system of claim 1, wherein the blade elements are formed on the exhaust hole.

3. The cooling system of claim 1, wherein the gantry comprises a rotor that rotates with the bore as a center, and a stator that is stationary, and the part box is mounted in the rotor.

4. The cooling system of claim 1, further comprising an exhaust fan formed together with the blade elements.

5. A cooling system of a computed tomography (CT) system, comprising:
   a gantry having a bore therein; and
   a table that moves into and out of the bore of the gantry,
   wherein the gantry comprises a part box mounted therein, and blade elements that are formed in regions of the part box are arranged to control an air flow inside the gantry,
   wherein the gantry comprises a rotor that rotates with the bore as a center, and a stator that is stationary, and the part box is mounted in the rotor, and
   wherein the blade elements comprise:
   a first blade element formed in the rotor; and
   a second blade element formed in the stator.

6. The cooling system of claim 5, wherein the first blade element is directly formed on the part box or a housing of the rotor.

7. A method of cooling a computed tomography CT system having a gantry including a rotor, a stator and a part box arranged within the rotor, the method comprising:
   activating exhaust fans mounted in the gantry to cool the gantry during a stand-by mode when the rotor of the gantry is not rotating; and
   cooling the gantry during an operating mode when the rotor is rotating to control air flow inside the gantry by blade elements formed inside the gantry,
   wherein the part box is an external housing for a part,
   wherein the part comprises one or more of an X-ray generator, an X-ray detector, a data acquisition system (DAS), a power supplier, a heat exchanger (HX), an high voltage generator (HVG),or a wireless transducer for each part box,
   wherein the part box comprises an inlet hole and an exhaust hole arranged in one or more surfaces of the part box,
   wherein the blade elements formed in the gantry include:
   fixing the blade elements on an inner surface of the part box,
   exposing one edge of each of the blade elements at a surface of the part box through the inlet hole, and
   extending another edge of each of the blade elements toward an inner side of the inlet hole of the part box, and
   wherein an extended portion between the one edge and the another edge in each of the blade elements is not visible through the inlet hole of the part box.

8. The method of claim 7, wherein the exhaust fans are formed together with at least one of the blade elements.

9. The method of claim 7, wherein during an operating mode all of the exhaust fans are deactivated.

10. The method of claim 7, wherein during an operating mode at least one of the exhaust fans is active to provide additional cooling to the gantry.

11. The method of claim 7, wherein during an operating mode at least some of the exhaust fans are active to provide additional cooling to the gantry.

12. A method of cooling a computed tomography CT system having a gantry including a rotor, a stator and a part box arranged within the rotor, the method comprising:
   activating exhaust fans mounted in the gantry to cool the gantry during a stand-by mode when the rotor of the gantry is not rotating; and
   cooling the gantry during an operating mode when the rotor is rotating to control air flow inside the gantry by blade elements formed inside the gantry,
   wherein the blade elements formed in the gantry include:
   forming a first blade element in the rotor; and
   forming a second blade element in the stator.

* * * * *